(12) United States Patent
Crowley et al.

(10) Patent No.: US 7,848,812 B2
(45) Date of Patent: Dec. 7, 2010

(54) ELECTIVE SERVICE INDICATOR BASED ON PULSE COUNT FOR IMPLANTABLE DEVICE

(75) Inventors: Tom Crowley, Lino Lakes, MN (US); Jeff Hagen, Plymouth, MN (US)

(73) Assignee: CVRx, Inc., Minneapolis, MN (US)

( * ) Notice: Subject to any disclaimer, the term of this patent is extended or adjusted under 35 U.S.C. 154(b) by 323 days.

(21) Appl. No.: 12/176,909

(22) Filed: Jul. 21, 2008

(65) Prior Publication Data
US 2009/0099625 A1    Apr. 16, 2009

Related U.S. Application Data

(60) Provisional application No. 60/951,114, filed on Jul. 20, 2007.

(51) Int. Cl.
*A61N 1/378* (2006.01)
*A61N 1/37* (2006.01)

(52) U.S. Cl. .......................... 607/29; 607/30

(58) Field of Classification Search .............. 607/30, 607/60, 29; 320/135–136
See application file for complete search history.

(56) References Cited

U.S. PATENT DOCUMENTS

| | | | |
|---|---|---|---|
| 4,556,061 A | 12/1985 | Barreras et al. | |
| 4,715,381 A | 12/1987 | Moberg | |
| 5,344,431 A * | 9/1994 | Merritt et al. | 607/29 |
| 5,402,070 A | 3/1995 | Shelton et al. | |
| 5,458,624 A | 10/1995 | Renirie et al. | |
| 5,741,307 A * | 4/1998 | Kroll | 607/5 |
| 5,769,873 A | 6/1998 | Zadeh | |
| 6,108,579 A | 8/2000 | Snell et al. | |
| 6,185,461 B1 | 2/2001 | Er | |
| 6,400,988 B1 | 6/2002 | Gurewitsch | |
| 6,584,355 B2 * | 6/2003 | Stessman | 607/29 |
| 6,654,640 B2 | 11/2003 | Lyden | |
| 6,671,552 B2 | 12/2003 | Merrit et al. | |
| 6,820,019 B1 | 11/2004 | Kelly et al. | |
| 6,901,293 B2 | 5/2005 | Rogers et al. | |
| 7,177,690 B2 | 2/2007 | Woods et al. | |

(Continued)

OTHER PUBLICATIONS

International Search Report, dated Jan. 29, 2009.

(Continued)

*Primary Examiner*—Carl H Layno
*Assistant Examiner*—Luther G Behringer
(74) *Attorney, Agent, or Firm*—Patterson Thuente Christensen Pedersen, P.A.

(57) ABSTRACT

The present invention is an implantable tissue stimulation therapy system, comprising an implantable tissue stimulation device including a power source of a known stored energy amount, a programmer communicably coupled to the device and adapted to propose one or more therapy parameters for the device, each therapy parameter having a known energy consumption associated therewith, wherein a predicted elective service date of the power source based on the one or more proposed therapy parameters and the known energy amount of the power source is automatically determined, and a display communicatively coupled to the activation device, the display being configured to indicate the predicted elective power source service date to an operator, wherein the operator may choose to select the one or more proposed therapy parameters based on the indicated predicted elective service date and the selected one or more therapy parameters are transmitted to the device.

35 Claims, 4 Drawing Sheets

U.S. PATENT DOCUMENTS

2003/0171791 A1   9/2003   KenKnight et al.
2005/0102005 A1   5/2005   Krig et al.
2005/0177206 A1*  8/2005   North et al. .................... 607/60
2006/0025829 A1   2/2006   Armstrong et al.
2007/0179547 A1   8/2007   Armstrong et al.

OTHER PUBLICATIONS

International Preliminary Report on Patentability, dated Feb. 4, 2010.

* cited by examiner

FIG. 4

ELECTIVE SERVICE INDICATOR BASED ON PULSE COUNT FOR IMPLANTABLE DEVICE

RELATED APPLICATION

The present application claims the benefit of U.S. Provisional Application No. 60/951,114, filed Jul. 20, 2007, the disclosure of which is incorporated by reference herein.

FIELD OF THE INVENTION

The present invention relates generally to implantable medical devices. More specifically, the present invention relates to a device and method for indicating when the power source of an implantable device is in need of service.

BACKGROUND OF THE INVENTION

Implantable medical devices typically rely on implanted power sources, such as a battery. Such batteries are commonly not rechargeable, and their life expectancy may be less than the life expectancy of the patient in which the device is implanted. Therefore the device may need to be explanted from the patient in order to change the power source. Determining the correct time to replace the battery is important for a number of reasons. Premature replacement can add unnecessary stress and trauma to the patient due to the surgery required to explant the device. However, delaying replacement of the battery could mean that the power source depletes to a level where the device cannot function as intended.

Cardiac pacemakers and implantable cardioverter-defibrillator (ICD) devices are two types of implantable medical devices that must function properly and reliably for patient survival, and there has been significant research and development in monitoring battery life for these types of devices. One of the challenges with monitoring battery life for pacemakers and ICDs is that these devices deliver variable therapies, often having an on-demand or as-needed therapy schedule. Because the therapies delivered by these devices are variable and not consistent over time, power consumption is unpredictable.

A number of methods have been used in the past to determine when to replace the battery in an implantable device such as a pacemaker or ICD. A first method of determining an elective replacement period is based on a "worst-case scenario" schedule. While such a replacement period is simple to calculate, the device is often replaced very prematurely. The operating parameters of pacing devices and cardioverter-defibrillators may vary widely over the life of the device either because of physiological changes in the patient, or because of marked changes in the patient's activity or condition. Therefore, the power consumed by these devices can vary over the lifetime of the device. As a result, an undesirably wide margin of error in the battery life prediction (the worst-case scenario) must be used to guard against these eventualities, thereby forcing premature surgical replacement of the implanted device and its battery in many cases, with the attendant risks of complications to the patient.

Monitoring one or more parameters of the battery, such as voltage or impedance, is another method to determine the elective replacement period of an implantable device, although this method has one significant shortcoming. For batteries having certain battery chemistries such as lithium-based batteries, the voltage of the battery will commonly very slowly decline over time with only a slight variation in voltage until the battery nears the end of its useful life. As the battery nears the end of its useful life, the battery voltage will begin to decline at a greater rate, often dramatically with a sharp drop-off in voltage. Such a battery is advantageous as a source of power for an implantable device because the battery delivers such an assured relatively constant voltage over most of the useful life of the device. However, such a battery creates a problem for a battery longevity monitor using the voltage of the battery to determine the longevity of the battery. Since the battery voltage remains relatively constant over most of the life of the battery, it is difficult to predict whether the battery is in the early part of the relatively flat voltage curve or nearing the end of the relatively flat voltage curve. The difference, of course, can mean a dramatic difference in the predicted longevity of the battery.

A further drawback to monitoring battery voltage and/or impedance to determine battery life is that the tolerances in battery voltage measurements as well as battery impedance may have such a wide variance in tolerances so as to render meaningless any estimation for battery replacement based on measurements of small changes in these values. Many implantable devices are thus prematurely explanted based upon these inadequate measurements.

Another method of determining replacement time of an implantable device such as a pacemaker is by measuring the energy consumed by the device. Since the battery energy at the time of implantation is known, circuitry can be included to subtract the energy consumed from the initial amount of energy to provide an approximate end of life for the battery. The basic concept of detecting end-of-life (EOL) by accumulating a measure of energy usage in an implanted pacemaker is illustrated in U.S. Pat. Nos. 4,556,061 and 4,715,381.

In U.S. Pat. No. 4,556,061, the invention relies on circuitry having an extremely precise capacitor to obtain an end of life for the battery. The device includes a counter which continuously accumulates the emitted pulses so as to provide a measure of the integral of battery current flow, and thus total energy expenditure. Unfortunately, the expected variability of the capacitor value over the lifetime of an implanted pacemaker, which may be ten or more years, leads to a loss of accuracy in the prediction of an appropriate time for battery replacement.

U.S. Pat. No. 4,715,381 illustrates a technique of making calculations of approximate battery energy expenditure, rather than actually measuring battery consumption. This reference shows a stimulation pulse counter which counts the number of delivered stimulus pulses. This information is utilized together with the programming parameters to determine the total amount of energy of the delivered pulses over an elapsed time. This calculated signal is added to a fundamental consumption signal which is based upon certain approximations and assumptions, and used to derive a signal representative of approximate total battery expenditure. This technique clearly provides at best an approximation, and is inherently subject to a greater probability of inaccuracy than the energy consumption technique. Further, this invention requires entering a "test mode" to determine end of battery life.

Another method of determining a battery replacement date is disclosed in U.S. Pat. No. 6,901,293, whereby a battery voltage monitor is combined with an energy counter. The device uses the data received from both a battery voltage monitor and an energy counter to determine an estimated battery replacement date.

A need still exists for an improved way of determining a battery replacement or recharging date for implantable medical devices such as therapy devices and monitoring devices.

SUMMARY OF THE INVENTION

In one embodiment, the present invention is a method of programming a tissue stimulation therapy device based on an elective power source service date. The method comprises providing a programmer, providing a display, and providing an implantable tissue stimulation therapy device having a power source of a known energy amount, with the device communicably coupled to the programmer and the display. The programmer is used to propose one or more therapy parameters for the device with the programmer, with each therapy parameter having a known energy consumption associated therewith. A predicted elective service date of the power source based on the one or more proposed therapy parameters and the known energy amount of the power source is automatically determined. A display is used to indicate the predicted elective power source service date to an operator, and in response to the operator reviewing the indicated predicted elective power source service date and selecting the one or more proposed therapy parameters based on the indicated predicted elective service date, the selected one or more therapy parameters are transmitted to the device.

In another embodiment, the present invention is an implantable tissue stimulation therapy system, comprising an implantable tissue stimulation device including a power source of a known stored energy amount, a programmer communicably coupled to the device and adapted to propose one or more therapy parameters for the device, each therapy parameter having a known energy consumption associated therewith, wherein a predicted elective service date of the power source based on the one or more proposed therapy parameters and the known energy amount of the power source is automatically determined, and a display communicatively coupled to the activation device, the display being configured to indicate the predicted elective power source service date to an operator, wherein the operator may choose to select or decline the one or more proposed therapy parameters based on the indicated predicted elective service date and the selected one or more therapy parameters are transmitted to the device.

In one embodiment, the present invention is a method of operating a programmable implantable tissue stimulation device having a power source of a known energy amount, comprising proposing one or more proposed therapy parameters to the device with a programmer, with each proposed therapy parameter having a known energy consumption associated therewith, automatically predicting an elective service date of the power source based on the one or more proposed therapy parameters and the known energy amount of the power source, indicating to an operator the predicted elective service date of the power source with a display, reviewing the predicted elective service date of the power source and selecting or declining the one or more proposed therapy parameters based on the indicated predicted elective service date, and transmitting the selected therapy parameters to the device.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

In the following detailed description of the present invention, numerous specific details are set forth in order to provide a thorough understanding of the present invention. However, it will be apparent to one skilled in the art that the present invention may be practiced without these specific details. In other instances, well-known methods, procedures, and components have not been described in detail so as to not unnecessarily obscure aspects of the present invention.

The present invention is suitable for use with various medical devices such as tissue stimulation devices, systems and methods, as well as monitoring devices. Tissue stimulation therapies can be used to stimulate nerves, including nerve endings and other neural structures, or receptors, such as baroreceptors, pressoreceptors, mechanoreceptors, stretch receptors and chemoreceptors, or other excitable tissues, or any other tissue of a patient. Although many of the embodiments described herein refer to stimulating tissues such as baroreceptors associated with the cardiovascular system, the present invention is also suitable for use with embodiments wherein cranial tissues, deep brain tissues, or spinal tissues are stimulated or other tissues. Tissue stimulation can be useful for treating various maladies and conditions, including but not limited to pain, sleep disorders, hypertension, hypotension, and other conditions.

To address hypertension, heart failure and their associated cardiovascular and nervous system disorders, a number of devices, systems and methods exist by which the blood pressure, nervous system activity, and neurohormonal activity may be selectively and controllably regulated by activating a patient's baroreflex system. By selectively and controllably activating baroreceptors, such devices, systems and methods reduce excessive blood pressure, sympathetic nervous system activation and neurohormonal activation, thereby minimizing their deleterious effects on the heart, vasculature and other organs and tissues.

In general, cardiovascular receptors may be sensitive to pressure and/or mechanical deformation and are referred to as baroreceptors, mechanoreceptors, pressoreceptors, stretch receptors, and the like. For cardiovascular and renal therapies, the present invention is intended to activate or otherwise interact with any or all of these types of receptors and/or nerve fibers from the receptors so long as such activation or interaction results in modulation of the reflex control of the patient's circulation. While there may be small structural or anatomical differences among various receptors in the vasculature, for the purposes of the present invention, activation may be directed at any of these receptors and/or nerves and/or nerve endings from these receptors so long as they provide the desired effects. In particular, such receptors will provide afferent signals, i.e., signals to the brain, which provide the blood pressure and/or volume information to the brain. This allows the brain to cause "reflex" changes in the autonomic nervous system, which in turn modulate organ activity to maintain desired hemodynamics and organ perfusion. For convenience, the term "baroreceptor" will be used to refer to any or all of such receptors, in the arterial or venous systems, unless otherwise expressly noted. Stimulation of the baroreflex system may be accomplished by stimulating such receptors, nerves, nerve fibers, or nerve endings, or any combination thereof.

Various devices, systems, and methods associated with exemplary baroreflex therapies are disclosed in, for example, U.S. Pat. No. 6,522,926 to Kieval et al., the disclosure of which is hereby incorporated by reference in its entirety.

One form of tissue stimulation therapy is an open loop therapy, that is, the therapy does not rely on continuous feedback to adjust one or more parameters of the therapy. The therapy may be monitored by one or more sensors, however the therapy is not adjusted in real-time based on information received from the sensor. Rather, the therapy is programmed by a physician and the therapy is delivered for a period of time, for example one month. The patient then returns to the physician, who may adjust one or more parameters of the therapy after examining the patient.

Figure 1:
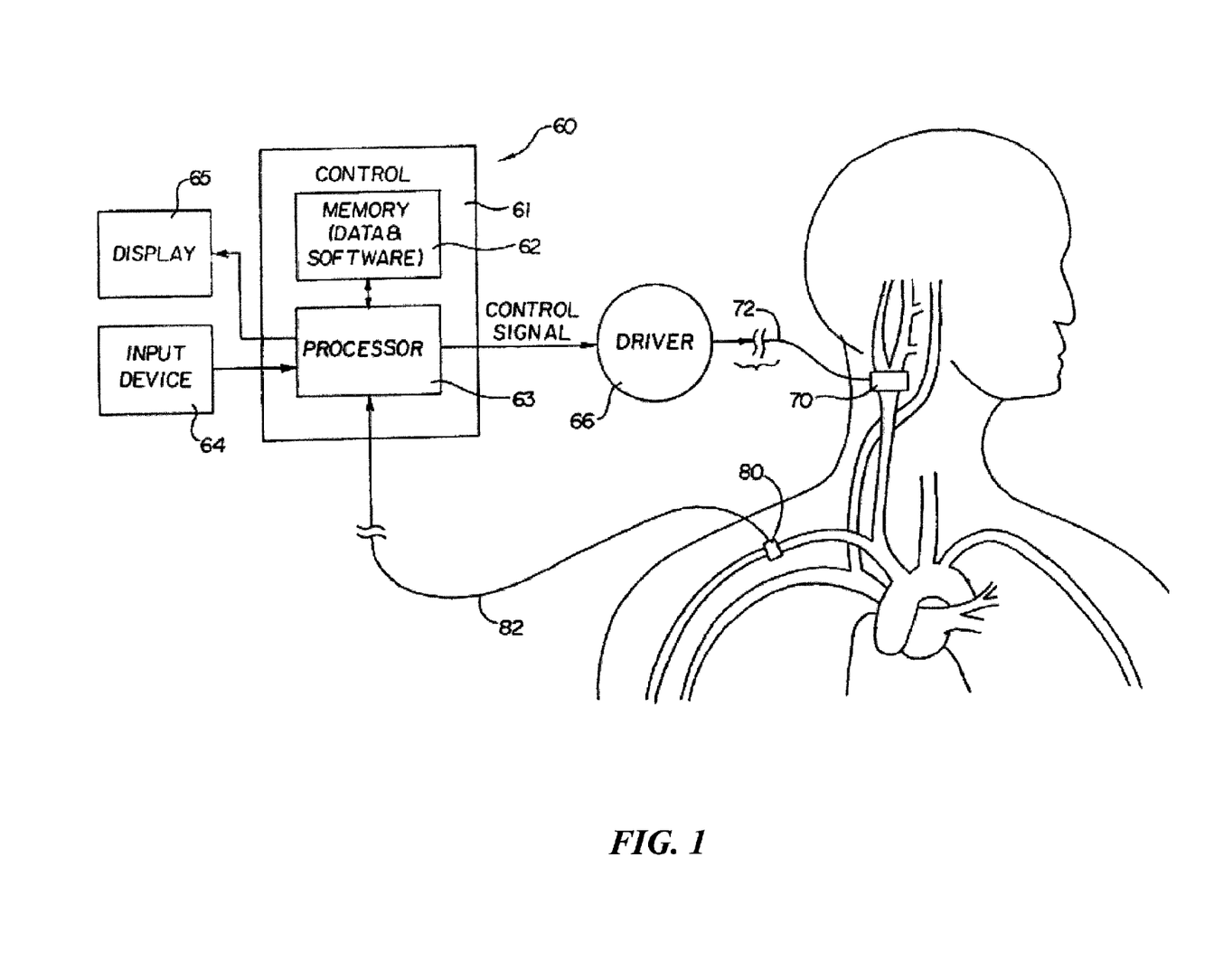
FIG. 1 is a schematic representation of one aspect of the present invention.

Typically, an implantable tissue stimulation therapy system includes a control system 60 coupled to a tissue stimulation device 70. By way of example, the control system 60 includes a control block 61 comprising a processor 63 and a memory 62. In one embodiment, the tissue stimulation therapy system comprises a baroreflex therapy system, and the tissue stimulation device 70 comprises a baroreflex activation device, as depicted in FIG. 1. In other embodiments, the tissue stimulation therapy device may comprise a cranial, spinal, or other neurostimulator or nerve therapy device.

Referring to FIG. 1, the control system 60 transmits a control signal to the baroreflex activation device. Control system 60 is connected to the sensor 80 by way of sensor cable 82. Control system 60 is also connected to the baroreflex activation device 70 by way of electric control cable 72. Thus, the control system 60 receives a sensor signal from the sensor 80 by way of sensor cable 82, and transmits a control signal to the baroreflex activation device 70 by way of control cable 72. In some instances, control system 60 includes a driver 66 to provide the desired power mode for the baroreflex therapy device 70. The electrical control signal generated by control system 60 may be continuous, periodic, episodic or a combination thereof, as dictated by an algorithm contained in the memory 62 of control system 60. Continuous control signals include a constant pulse, a constant train of pulses, a triggered pulse and a triggered train of pulses. Periodic control signals include each of the continuous control signals described above which have a designated start time and a designated duration. Episodic control signals include each of the continuous control signals described above which are triggered by an episode.

The memory 62 may contain data related to the sensor signal, the control signal, and/or values and commands provided by the programmer 64. The memory 62 may also include software containing one or more algorithms defining one or more functions or relationships between the control signal and the sensor signal. The algorithm may dictate activation or deactivation control signals depending on the sensor signal or a mathematical derivative thereof. The algorithm may dictate an activation or deactivation control signal when the sensor signal falls below a lower predetermined threshold value, rises above an upper predetermined threshold value or when the sensor signal indicates a specific physiologic event.

The control signal activates, deactivates or otherwise modulates the baroreflex activation device. In electrical activation embodiments using a non modulated signal, the output (power or energy) level of the baroreflex activation device may be changed by adjusting parameters such as the output signal voltage level, current level and/or signal duration. The output signal of the baroreflex activation device may be, for example, constant current or constant voltage. In electrical activation embodiments using a modulated signal, wherein the output signal comprises, for example, a series of pulses, several pulse characteristics may be changed individually or in combination to change the power or energy level of the output signal. Such pulse characteristics or parameters include, but are not limited to: pulse amplitude (PA), pulse frequency (PF), pulse width or duration (PW), pulse waveform (square, triangular, sinusoidal, etc.), pulse polarity (for bipolar electrodes) and pulse phase (monophasic, biphasic).

A number of the parameters of the control signal and/or the output signal can be adjusted or modified by a physician in order to tailor the baroreflex therapy as desired. Adjusting one or more of the parameters may, and often does, have an effect on the amount of energy consumed by the power source which in turn has an effect on the estimated life of the power source.

Once the parameters of the therapy are set by a physician in an open loop therapy, the energy consumption of the baroreflex therapy device will remain constant until the parameters are later adjusted (if necessary). The amount of energy consumption can then be accurately predicted, and an elective service date of the power source determined therefrom. In one embodiment of the present invention, the service date comprises a replacement date for the power source. In another embodiment having a rechargeable power source, the service date of the power source comprises a charging date. The length of time between charges may be selected so as to be beneficial to longevity of the power supply. In one embodiment, an estimated charging date is determined so as to maximize the amount of time between charges. In one embodiment, the estimated charging date is determined based on one or more parameters of the power source, such as when the output voltage of the power source begins to rapidly decline.

In addition to the parameters programmed into the therapy, the characteristics of the therapy device itself will have an effect on battery longevity. In one embodiment, the present invention interrogates the baroreflex therapy device to determine the impedance of one or more leads coupled to the therapy device. Based on the impedance of the lead and/or other device characteristics, and the parameters of the therapy, the power source longevity can be calculated and an estimated battery service date can be determined.

The predicted elective service date indicated, such as by a display 65, may be offset from the actual estimated end of power source life. For example, the service date may be shown as being one month before the actual end of battery life. In this way, a margin of safety is included in the indicated service date, allowing a cushion of time to service the battery before it is completely drained. In one embodiment, the display 65 simulates a countdown by indicating an elapsed time until power source service is required.

In one embodiment, a counter increments the total energy consumed to date on a periodic basis, thereby updating the estimated battery replacement date. The period may be in terms of hours, days, months, or other suitable length as apparent to one skilled in the art.

In another embodiment, the baroreflex therapy comprises a closed loop therapy. In such an embodiment, control system 60 includes one or more sensors 80 to provide feedback on one or more parameters associated with the delivered therapy. Such parameters may include patient physiologic parameters or responses, device parameters, or other parameters indicative of the efficacy of the therapy. Control system 60 includes an algorithm contained in memory 62 that is configured to predict future energy usage of the baroreflex therapy device based on past energy usage and one or more programmed parameters.

Patient physiologic parameters to be measured by sensor 80 may include cardiac activity, cardiac electrical activity such as ECG, blood pressure (systolic, diastolic, average or pulse pressure), blood volumetric flow rate, blood flow velocity, heart rate, respiration rate, vessel dilation or constriction, heart or body movement, patient activity levels, patient orientation, blood pH, blood O2 or CO2 content, mixed venous oxygen saturation (SVO2), vascular impedance or other tissue impedance, vasoactivity, nerve activity, nerve traffic, tissue activity or composition. Examples of suitable devices, transducers, or gauges for sensor 80 include ECG electrodes (near-field or far-field), a piezoelectric pressure transducer, an ultrasonic flow velocity transducer, an ultrasonic volumetric flow rate transducer, a thermodilution flow velocity transducer, a capacitive pressure transducer, a membrane pH electrode, an optical detector (SVO2), accelerometer or a strain gage. Although only one sensor 80 is shown, multiple sensors 80 of the same or different type at the same or different locations may be utilized.

In addition to patient parameters, certain device parameters may also be measured, including lead impedance, therapy current, or therapy voltage. Other parameters that can be measured may include environmental parameters such as time, temperature, atmospheric pressure, and so forth.

Figure 2:
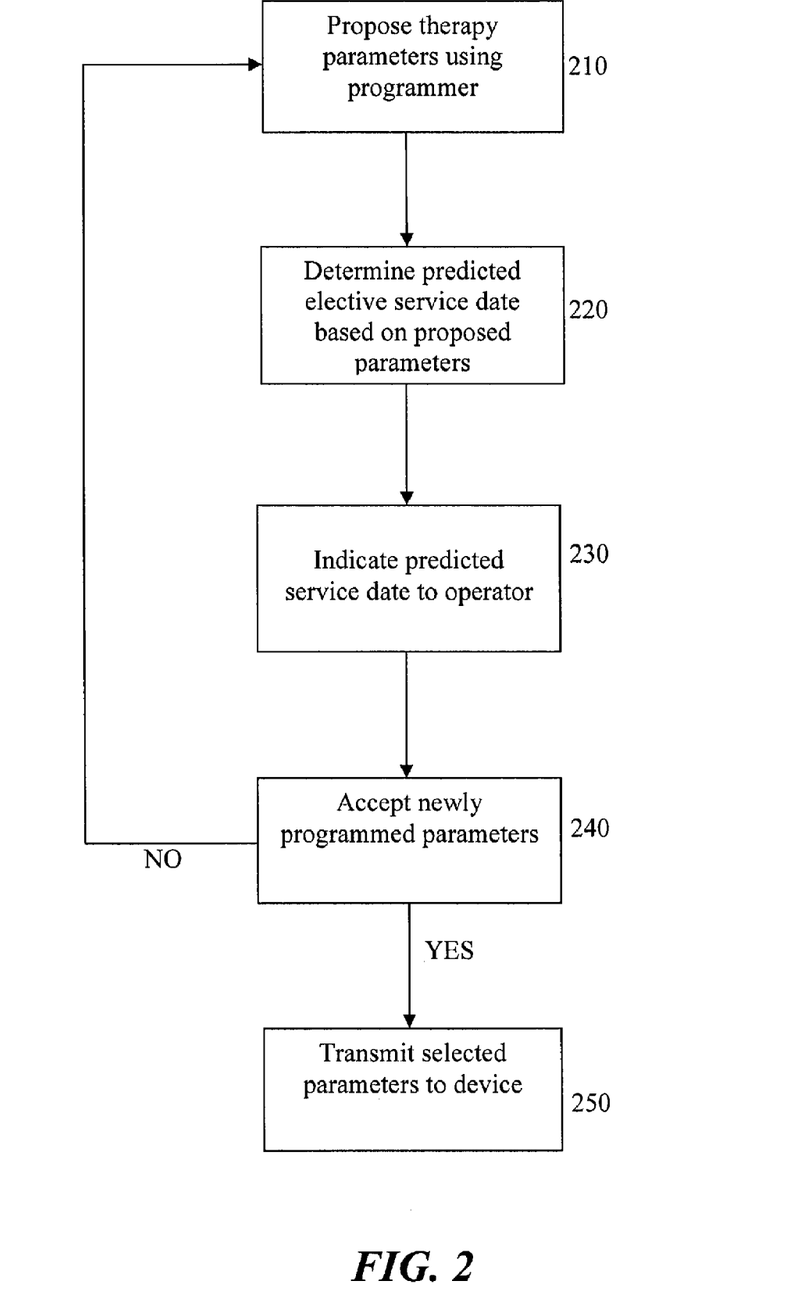
FIG. 2 is an operational flowchart of one aspect of the present invention.

Referring now to FIG. 2, an operational flowchart of one aspect of the present invention is depicted. An operator such as a physician uses the programmer or input device to propose one or more therapy parameters in 210. A predicted elective service date based on the proposed one or more therapy parameters is determined in 220. The predicted elective service date is indicated to the operator in 230. The operator can accept, decline, or modify the one or more proposed therapy parameters in 240. If the proposed parameters are accepted, the parameters are transmitted to the device in 250. If the proposed parameters are declined, the original power source service date is indicated to the operator. In one embodiment, the operator is given immediate indication of how the proposed changes to the therapy parameters will affect power source longevity, therapy efficacy, or both. The indication of the service date may be accomplished by an auditory indication, or visual indication such as a display, series of lights, or other.

In one embodiment, one or more therapy parameters are selected by an operator to optimize battery life. In another embodiment, one or more therapy parameters are selected by an operator to optimize therapy efficacy. In a further embodiment, one or more therapy parameters are selected by an operator to balance battery longevity with therapy efficacy.

Figure 3:
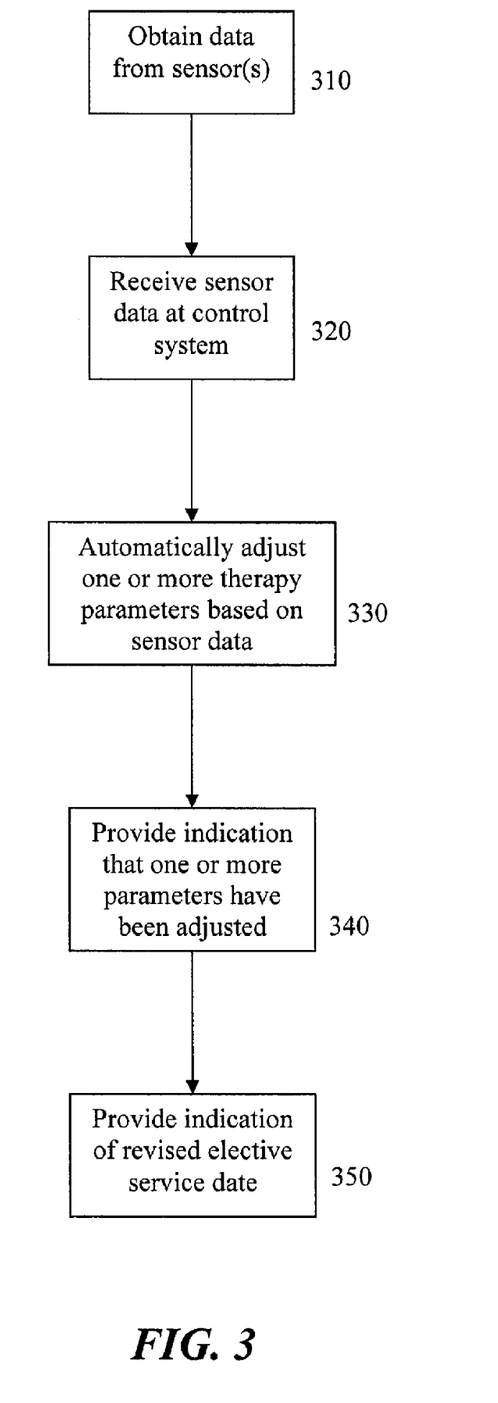
FIG. 3 is an operational flowchart of another aspect of the present invention.

In another embodiment depicted in FIG. 3, control system 60 is configured to operate in a closed-loop auto-adjust mode so as to automatically select parameters to optimize battery life, or optimize therapy efficacy, or both, by using processor 63 and/or an algorithm contained in memory 62. In 310, sensor 80 may obtain data indicative of one or more parameters and transmit the data to control system 60 in 320. Control system 60 may rely on data received from one or more sensors 80 in selecting therapy parameters for a desired purpose (such as battery longevity or therapy efficacy) in 330. In another embodiment, control system 60 may adjust one or more therapy parameters during the therapy to attain or maintain a desired result, such as battery longevity or therapy efficacy. Such adjustment may be based on data received from one or more sensors 80. In 340, display 65 may include an indication that one or more therapy parameters has been adjusted by control system 60. In 350, display 65 may include an indication that the indicated predicted elective service date has changed to reflect the auto-adjustment by control system 60. In a further embodiment, control system 60 stores a log of each time a therapy parameter has been adjusted or modified. The log may be manually retrieved at any time, or automatically reported to an operator on a periodic basis.

In one embodiment, the present invention is configured to perform a dose-response test to predict the efficacy of a baroreflex therapy at different settings. The dose-response test can be manually requested by a physician or patient, or the test can be automatically requested and performed by the device. The results of such a test can then be viewed by an operator for use in selecting baroreflex therapy parameters. Alternatively, the results of a dose-response test can be provided to a control system of the device, which uses an algorithm to select therapy parameters based on the test results. In another embodiment, a strength-duration curve is generated to predict the efficacy of a baroreflex therapy, and the curve is used to select one or more parameters for the therapy. In another embodiment, the predicted power source longevity is combined with the results of the dose-response test to optimize the therapy.

Figure 4:
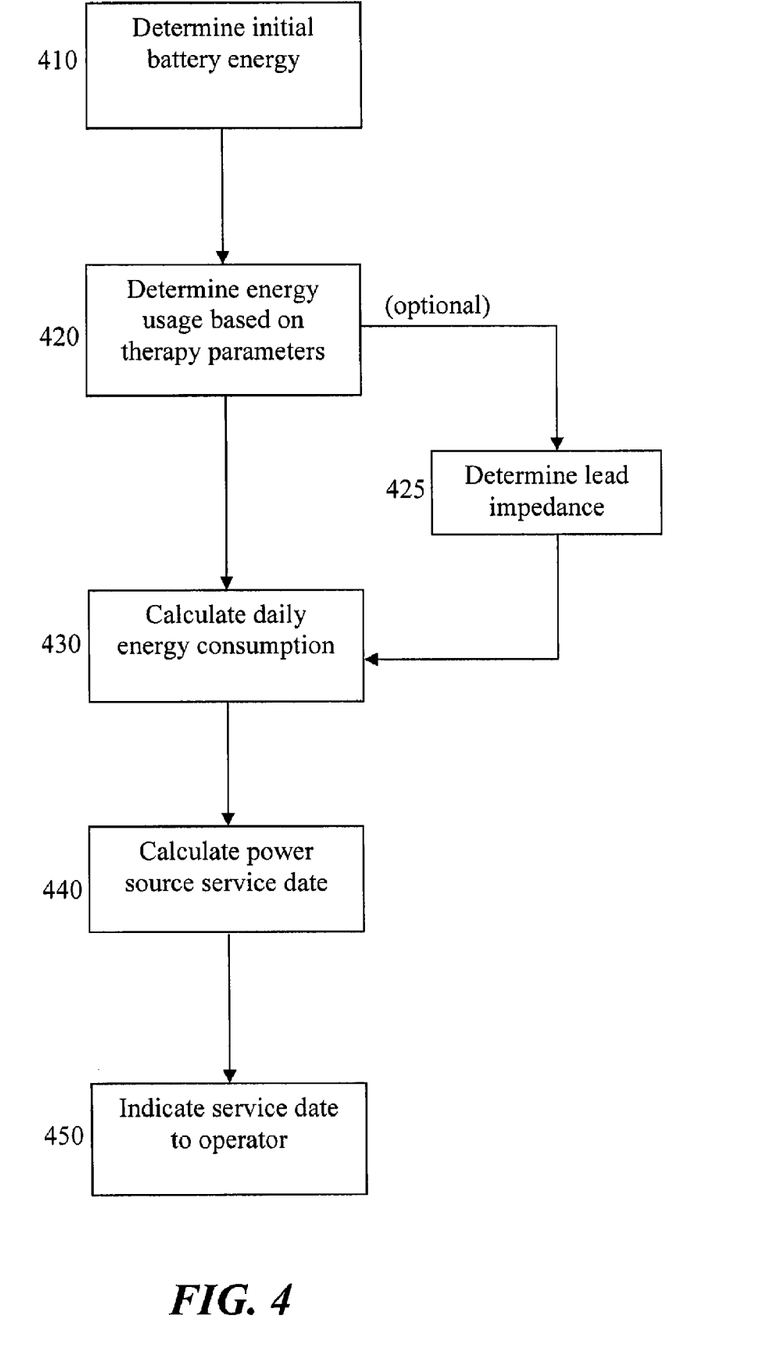
FIG. 4 is an operational flowchart of another aspect of the present invention.

Referring now to FIG. 4, a flowchart is depicted illustrating a method of determining a battery service date of an implanted tissue stimulation therapy device according to one aspect of the present invention. In 410, the amount of energy contained in the battery at the beginning of its life is known or determined. In one embodiment of 410, the amount of energy in the battery at the beginning of a given programming or interrogation session is either known or determined. One or more programmed therapy parameters are associated with operation of the therapy device, with each of the parameters having an energy consumption associated therewith, which is determined in 420. In one embodiment, the impedance of one or more leads coupled to the tissue stimulation therapy device is determined in 425. Energy consumption for a given period (such as one day) is calculated in 430, based on the results of 420 and optionally 425.

As an example, in one embodiment wherein the tissue stimulation therapy comprises delivered pulses, the amount of energy consumed for each pulse can be determined in 420. The number of times the therapy is delivered for a given period is known or can be determined, and is used to calculate the energy consumption for a given period in 430. This periodic energy consumption is compared to the known energy amount of the battery from 410 to calculate the useful lifespan of the battery, and from that, an elective service date, in 440. In one embodiment, the useful lifespan comprises the time when a rechargeable battery will be drained and need to be charged. In another embodiment, the useful lifespan comprises the time when a battery must be replaced. The elective service date may be the calculated end of useful life of the battery, or may be offset by some period of time to create a safety factor. The predicted elective service date of the battery is indicated to an operator in 450.

In one embodiment, the present invention is applicable to medical devices such as monitoring devices. Monitoring devices may be programmed to obtain data at specific intervals, and store the data for review or export at a later time. Such a monitoring device may exhibit similar power source energy consumption characteristics to the tissue stimulation devices discussed herein, allowing a predicted elective power source service date to be determined for a monitoring device.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. A method of programming a tissue stimulation therapy device based on an elective power source service date, comprising:
   providing a programmer;
   providing a display;
   providing an implantable tissue stimulation therapy device having a power source of a known energy amount, the device communicably coupled to the programmer and the display, wherein the tissue stimulation therapy device comprises a baroreflex activation device;
   proposing one or more therapy parameters for the device with the programmer, each therapy parameter having a known energy consumption associated therewith;
   automatically determining a predicted elective service date of the power source based on the one or more proposed therapy parameters and the known energy amount of the power source;
   providing an indication of the predicted elective power source service date to an operator with the display; and
   in response to the operator reviewing the indicated predicted elective power source service date and selecting the one or more proposed therapy parameters based on the indicated predicted elective service date, transmitting the selected one or more therapy parameters to the device.

2. The method of claim 1, further comprising:
   providing a lead coupled to the implantable medical device;
   determining the impedance of the lead; and
   automatically predicting a useful lifespan of the power source based on the impedance of the lead, the one or more proposed therapy parameters, and the known energy amount of the power source.

3. The method of claim 1, wherein the operator selecting the one or more proposed therapy parameters based on the indicated predicted elective service date comprises selecting the one or more therapy parameters to optimize longevity of the power source.

4. The method of claim 1, further comprising delivering a therapy with the device, the therapy having at least one selected therapy parameter.

5. The method of claim 4, further comprising:
   measuring at least one physiologic patient response to the delivered therapy and communicating data indicative of the patient response to the programmer; and
   adjusting one or more therapy parameters with the programmer based on the data indicative of the patient response.

6. The method of claim 5, wherein adjusting one or more therapy parameters comprises adjusting one or more therapy parameters to optimize longevity of the power source.

7. The method of claim 5, wherein adjusting one or more therapy parameters comprises adjusting one or more therapy parameters to optimize efficacy of the therapy.

8. The method of claim 5, wherein adjusting one or more therapy parameters comprises adjusting one or more therapy parameters to balance longevity of the power source with efficacy of the therapy.

9. The method of claim 5, wherein adjusting the one or more therapy parameters with the programmer comprises automatically adjusting the one or more therapy parameters.

10. The method of claim 4, further comprising:
    measuring at least one device parameter related to the delivered therapy and communicating data indicative of the device parameter to the programmer; and
    adjusting one or more therapy parameters with the programmer based on the data indicative of the device parameter.

11. The method of claim 1, wherein the predicted elective power source service date comprises a recharging date.

12. The method of claim 1, wherein the predicted elective power source service date comprises a replacement date.

13. An implantable tissue stimulation therapy system comprising:
    an implantable tissue stimulation device including a power source of a known stored energy amount, wherein the implantable tissue stimulation device comprises a baroreflex activation device;
    a programmer communicably coupled to the device and adapted to propose one or more therapy parameters for the device, each therapy parameter having a known energy consumption associated therewith, wherein a predicted elective service date of the power source based on the one or more proposed therapy parameters and the known energy amount of the power source is automatically determined;
    a sensor operably coupled to the programmer, the sensor adapted to measure at least one physiologic patient response to a delivered therapy having one or more of the selected therapy parameters; and
    a display communicatively coupled to the stimulation device, the display being configured to provide an indication of the predicted elective power source service date to an operator, wherein the operator may choose to select the one or more proposed therapy parameters based on the indicated predicted elective service date and the selected one or more therapy parameters are transmitted to the device.

14. The system of claim 13, wherein the programmer is configured to adjust one or more therapy parameters based on the measured at least one physiologic patient response.

15. The system of claim 13, further comprising a lead coupled to the therapy device, the lead having a determinable impedance, wherein a predicted elective service date of the power source is automatically predicted based on the impedance of the lead, the one or more proposed therapy parameters, and the known energy amount of the power source.

16. A method of operating an implantable therapy system, comprising:
    providing a programmer;
    providing a display;

providing an implantable tissue stimulation therapy device having a power source of a known energy amount, the device communicably coupled to the programmer and the display wherein the tissue stimulation therapy device comprises a baroreflex activation device;

providing instructions for programming the therapy device, comprising:

using the programmer to propose one or more therapy parameters for the device, each therapy parameter having a known energy consumption associated therewith;

automatically determining a predicted elective service date of the power source based on the one or more proposed therapy parameters and the known energy amount of the power source;

using the display to indicate the predicted elective power source service date to an operator;

in response to reviewing the indicated elective power source service date and confirming the one or more proposed therapy parameters based on the indicated predicted elective service date, transmitting the selected one or more therapy parameters to the device.

17. The method of claim 16, further comprising:
providing a lead coupled to the therapy device;
determining the impedance of the lead; and
automatically predicting an elective service date of the power source based on the impedance of the lead, the one or more proposed therapy parameters, and the known energy amount of the power source.

18. The method of claim 16, further comprising delivering with the device a therapy having at least one of the selected therapy parameters.

19. The method of claim 18, further comprising:
measuring at least one physiologic patient response to the delivered therapy; and
using the programmer to adjust one or more therapy parameters based on the at least one measured physiologic patient response.

20. The method of claim 16 or 19, wherein using the programmer to adjust one or more therapy parameters comprises adjusting one or more therapy parameters to optimize longevity of the power source.

21. The methods of claim 16 or 19, wherein using the programmer to adjust one or more therapy parameters comprises adjusting one or more therapy parameters to optimize efficacy of the therapy.

22. The methods of claim 16 or 19, wherein using the programmer to adjust one or more therapy parameters comprises adjusting one more therapy parameters to balance longevity of the power source with efficacy of the therapy.

23. The method of claim 19, wherein adjusting the one or more therapy parameters with the programmer comprises automatically adjusting the one or more therapy parameters.

24. The method of claim 18, wherein using the programmer to adjust one or more therapy parameters comprises automatically adjusting one or more therapy parameters.

25. The method of claim 16, further comprising:
measuring at least one device parameter related to the delivered therapy and communicating data indicative of the device parameter to the programmer; and
adjusting one or more therapy parameters with the programmer based on the data indicative of the device parameter.

26. The method of claim 16, wherein the predicted elective power source service date comprises a recharging date.

27. The method of claim 16, wherein the predicted elective power source service date comprises a replacement date.

28. A method of operating a programmable implantable baroreflex activation device having a power source of a known energy amount, comprising:
proposing one or more therapy parameters to the device with a programmer, each proposed therapy parameter having a known energy consumption associated therewith;
automatically predicting an elective service date of the power source based on the one or more proposed therapy parameters and the known energy amount of the power source;
indicating to an operator the predicted elective service date of the power source with a display;
reviewing the predicted elective service date of the power source and selecting or declining the one or more proposed therapy parameters based on the indicated predicted elective service date; and
transmitting the selected therapy parameters to the device.

29. The method of claim 28, further comprising:
determining the impedance of a lead coupled to the implantable baroreflex activation device; and
automatically predicting an elective service date of the power source based on the impedance of the lead, the one or more proposed therapy parameters, and the known energy amount of the power source.

30. The method of claim 28, further comprising delivering with the implantable baroreflex activation device a therapy having at least one of the selected therapy parameters.

31. The method of claim 30, further comprising:
measuring at least one physiologic patient response to the delivered therapy; and
adjusting one or more therapy parameters with the programmer based on the at least one measured physiologic patient response.

32. The method of claim 31, wherein using the programmer to adjust one or more therapy parameters comprises adjusting one or more therapy parameters to optimize longevity of the power source.

33. The method of claim 31, wherein using the programmer to adjust one or more therapy parameters comprises adjusting one or more therapy parameters to optimize efficacy of the therapy.

34. The method of claim 31, wherein using the programmer to adjust one or more therapy parameters comprises adjusting one or more therapy parameters to balance longevity of the power source with efficacy of the therapy.

35. The method of claim 31, wherein adjusting the one or more therapy parameters with the programmer comprises automatically adjusting the one or more therapy parameters.

* * * * *